United States Patent [19]

Freiter

[11] 4,107,210

[45] Aug. 15, 1978

[54] SYNTHESIS OF ALPHA-DIKETONES

[75] Inventor: Edward R. Freiter, Midland, Mich.

[73] Assignee: The Dow Chemical Company, Midland, Mich.

[21] Appl. No.: 720,934

[22] Filed: Sep. 7, 1976

[51] Int. Cl.$^2$ ............................................. C07C 45/18
[52] U.S. Cl. .............. 260/590 E; 260/586 C; 260/595
[58] Field of Search ............... 260/590 R, 590 E, 595, 260/586 C, 593 R

[56] References Cited

U.S. PATENT DOCUMENTS

| | | | |
|---|---|---|---|
| 3,030,416 | 4/1962 | Mikusch-Buchberg | 260/595 |
| 3,240,811 | 3/1966 | Drysdale | 260/595 |
| 3,526,634 | 9/1970 | Adachi et al. | 260/471 R |

OTHER PUBLICATIONS

Huckin et al., Can. J. of Chem., vol. 52, pp. 1379–1380, (1974).

*Primary Examiner*—James O. Thomas, Jr.
*Assistant Examiner*—James H. Reamer
*Attorney, Agent, or Firm*—Michael S. Jenkins; James B. Guffey

[57] ABSTRACT

Alpha-diketones, such as 1-phenyl-1,2-propanedione and 1-propyl-1,2-butanedione, are prepared by reacting an acylmethyl ester of a carboxylic acid (e.g., benzoylmethyl acetate or butanoylmethyl propionate) with an aldehyde, such as formaldehyde or acetaldehyde, in the presence of an acid catalyst and water. Such alpha-diketones are also obtained by first refluxing a mixture of an alpha-haloketone and a carboxyl anion source and then reacting the mixture with an aldehyde in the presence of an acid catalyst and water.

18 Claims, No Drawings

SYNTHESIS OF ALPHA-DIKETONES

BACKGROUND OF THE INVENTION

This invention relates to processes for the preparation of alpha-diketones.

Alpha-diketones are valuable intermediates for pharmaceutical products, dyestuffs and perfumes and therefore a variety of methods for preparing such compounds have previously been suggested and employed. For example, alpha-diketones have been prepared by nitrosation of appropriate ketone derivatives followed by hydrolysis as illustrated by equations (1) and (2). V. Peckman, Ber., Vol. 21, Page 1411 (1888); Vol. 24, page 3954 (1891).

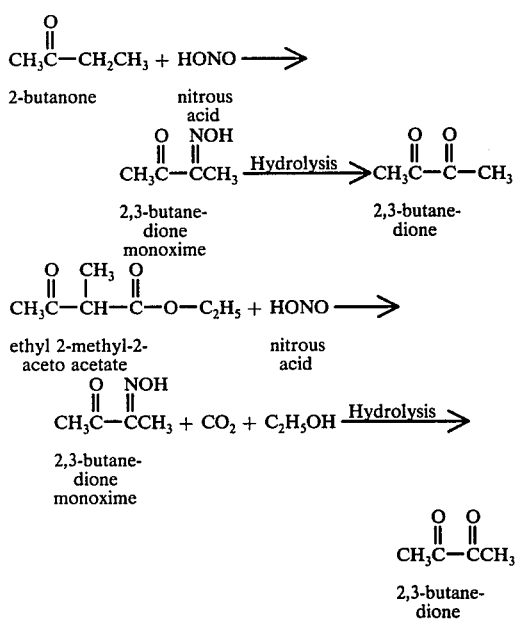

Various oxidation reactions, as exemplified by equations (3) through (9), have also been suggested.

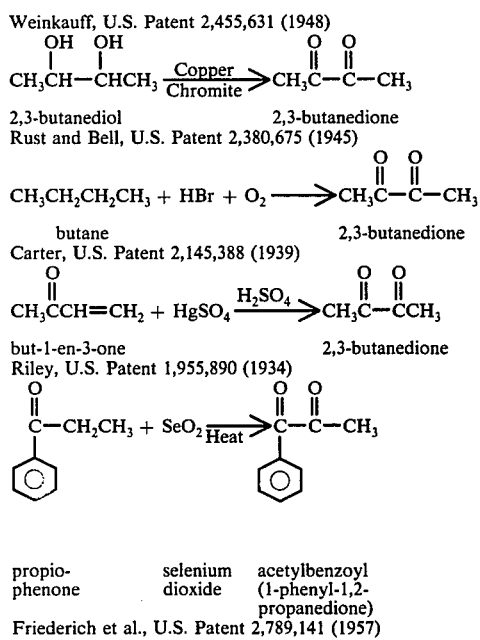

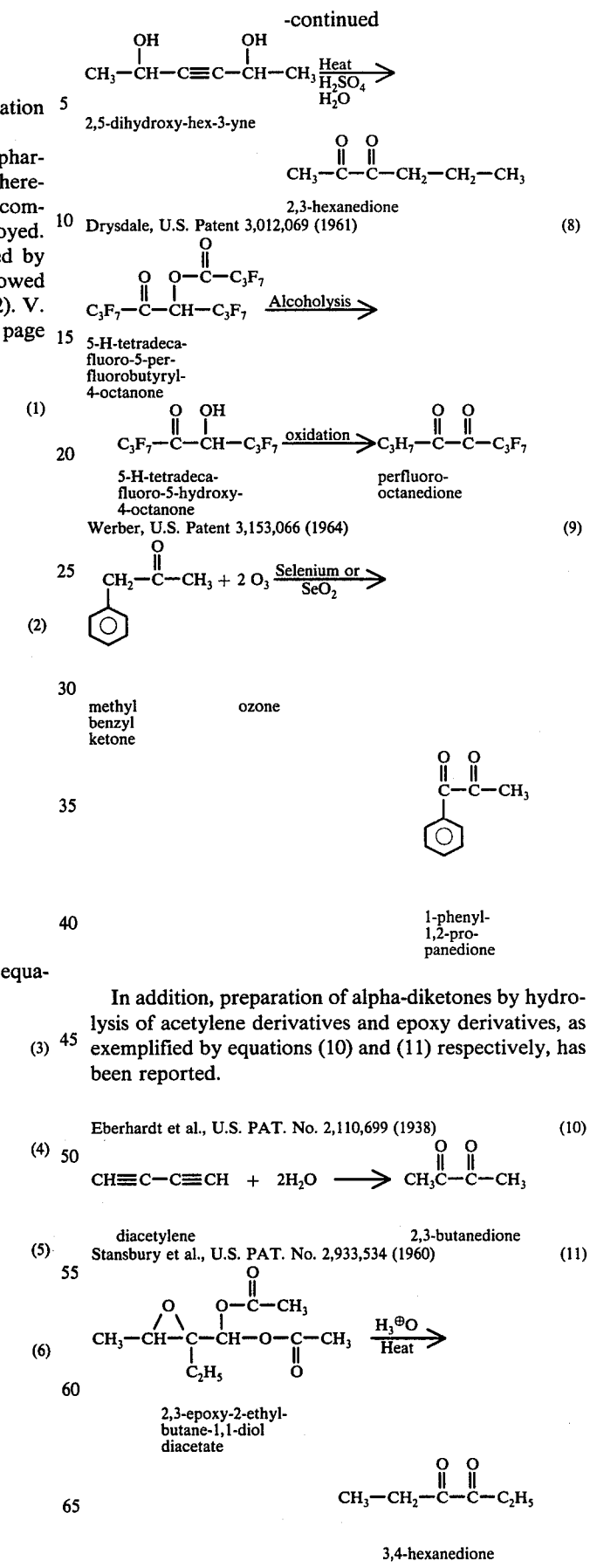

In addition, preparation of alpha-diketones by hydrolysis of acetylene derivatives and epoxy derivatives, as exemplified by equations (10) and (11) respectively, has been reported.

the portion 18 being headed to retain the insulating medium.

Returning to the example shown in FIG. 1, the free end of the sleeve 21 is resistance welded to the annular rim of a cup-shaped bridgingmember 23 formed from Inconel X750. The arrangement is such that the base 24 of the member 23 is spaced from the free end 25 of the portion 18 of the electrode rod 16 and trapped between the end 25 and the base 24 is a cylindrical heating element 26 which will be described in detail below. To locate the heating element 26 in position, recesses are formed in the end 25 and base 24 and the ends of the heating element 26 are shaped so as to be received in the recesses respectively, although in this example the heating element is not actually joined to the member 23 and rod 16. It is, however, to be appreciated that other ways of locating the heating element 26 can be employed, such as by providing recesses in the ends respectively of the heating element and complementary projections on the end 25 and the base 24. Also, the heating element 26 can be joined to the end 25 of the rod 16 and/or the base 24 of the member 23. Suitable methods of effecting such joints are by brazing and diffusion bonding, both of which techniques will be described below.

Engaged with the internal screw thread 14 is an annular mild steel, externally screw threaded stud 27 which traps an alumina tube 28 against the collar 22 by way of a steel or aluminium sealing washer 29. Conveniently, a further annular washer 31 formed frm asbestos or Fiberfrax is interposed between the washer 29 and the tube 28, with stud 27, the tube 28, the washer 29 and, where applicable, the washer 31 all extending around, but being spaced from, the electrode rod 16. Moreover, the stud 27 is provided with a slot 27a adapted to receive a screwdriver and is screwed into the portion 14 so that the tube 28 is forced against the thrust collar 22, which is of course secured to the electrode rod 16. Thus, the electrode rod 16 is urged towards the contact member 23 so that the heating element 26 is compressed between, and is urged into physical and electrical contact with, the electrode rod 16 and the contact member 23. In one practical embodiment, the electrode rod 16 is urged by the stud 27 to apply a compressive load of between 7.5 and 300 MN/m² to the heating element 26. When the stud 27 has been screwed into the body 11 by the required amount, the space between the electrode rod 16 and the stud 27, washer 29 and tube 28 is filled with an epoxy resin sealing compound 32. The compound 32 of course insulates the electrode rod 16 from the stud 27 and washer 29, and also prevents the escape of combustion gases through the end 12 of the body.

The heating element 26 is in the form of a sintered, electrically conducting, composite, refractory block and consists of a pair of end portions 33,34 and a central portion 35. The end portions 33, 34 define the electrical contacts of the heating element and are composed of sintered chromium powder mixed with some chromium oxide powder to prevent lamination. The central portion 35 defines the high resistance part of the heating element and is composed of sintered chromium oxide mixed with some chromium powder to render the portion 35 conductive.

The heating element 26 is produced by first wet ball milling chromium metal powder as supplied by Koch-Light Laboratories Limited as type 8941H for 2½ hours so as to reduce the mean Fisher particle size of the powder to between one and nine microns. The powder is then dried and sieved and is made into an aqueous slurry with chromic oxide powder which is supplied by Hopkins & Williams Limited as type 315400 and which has previously been dried and sieved and has a mean Fisher particle size of 0.7 microns. The slurry is arranged to contain 50% by volume of the chromium powder and 50% by volume of the chromium oxide powder, and is blended in a Z-Blade mixer together with 2% by weight of a binder in the form of Celacol M450 as supplied by British Celanese Limited. The mixer is fitted with a heating jacket so that, after mixing, the slurry is dried to form an intimately mixed powder, which is then passed firstly through a 500 micron sieve and then through a 250 micron sieve. The portion of the mixture retained by the latter sieve is retrieved and is heated in an oven to ensure that the powder is completely dry and free flowing. The powder mixture is to define the end portion 33, 34 of the heating element. The same procedure is repeated to produce the powder mixture required for the central portion 35, but in this case the slurry is arranged to contain 24% by volume of the chromium powder and 76% by volume of the chromic oxide powder.

Both sets of powder mixture are then lubricated by dry roll mixing with 0.5% by weight of magnesium stearate, whereafter 0.03gm of the high chromium content mixture is introduced into a cylindrical die cavity of 3mm diameter in a hardened steel, floating die. The die is arranged so that the axis of the die cavity is vertical and the sample of the high chromium content mixture is poured onto a first punch located 3mm from the top of the die. The arrangement is such that the powder mixture then fills the space above the first punch and, after removal of any surplus powder, the first punch is lowered by a distance of 7.5mm. A 0.06gm sample of the high chromium oxide content mixture is then introduced into the die cavity to fill the space above the powder already present, whereafter any surplus powder is removed and the first punch is lowered by a further 3mm. A further 0.03gm sample of the high chromium content mixture is then introduced into the die cavity and the resultant three layer mixture is pressed between the first punch and a second punch at an applied load of 550 MN/m². Each punch is recessed at its surface presented to the powder mixture so that the green compact produced by the pressing operation has the projections required for location of the final heating element 26 in the starting aid. In one particular example the recess in each punch is of conical form with the included angle of the cone being 140°.

After removal from the die cavity the green compact is heated in a dry, oxygen-free argon atmosphere at a rate 300° C per hour until a temperature of 1400° C is reached. The compact is held at this temperature for one hour and is then allowed to cool, the complete heating and cooling cycle taking 11 hours. The resultant sintered block is 94% of theoretical density and has resistance of between 0.11 and 0.19 ohm. However, by varying the amount of powder mixtures used to produce the green compact, it is possible to obtain sintered blocks having resistances between 0.1 and 0.7 ohm. Finally, the block is machined by a centreless grinding operation so as to produce the required heating element 26 having a diameter of 2mm and a resistance of between 0.12 and 0.20 ohm. Again, however, variation in the composition of the green compact enables different resistance values to be obtained, so that by employing the technique described above it is possible to produce ganic radicals as hereinafter defined. It is understood, of course, that R and R" may be different organic radicals in a given alpha-diketone product.

Examples of the aforementioned 1-substituted-1,2-propanediones include 1-methyl-1,2-propanedione, 1-ethyl-1,2-propanedione, 1-pentyl-1,2-propanedione, 1-cyclohexyl-1,2-propanedione, 1-phenyl-1,2-propanedione, 1-halophenyl-1,2-propanedione, 1-phenoxyphenyl-1,2-propanedione, 1-(ar-t-butylphenyl)-1,2-propanedione, 1-naphthyl-1,2-propanedione, etc.

Examples of the aforementioned 1,3-disubstituted-1,2-propanediones include 1-propyl-3-propyl-1,2-propanedione (i.e., 4,5-nonanedione), 1-tert-butyl-3-methyl-1,2-propanedione (i.e. 2,2-dimethyl-3,4-hexanedione), 1-cyclopentyl-3-ethyl-1,2-propanedione (i.e. 1-cyclopentyl-1,2-pentanedione), 1-halonaphthyl-3-cyclo-octyl-1,2-propanedione, 1,3-diphenyl-1,2-propanedione, 1-methyl-3-phenyl-1,2-propanedione (i.e. 1-phenyl-2,3-butanedione), 1-cyclohexyl-3-phenyl-1,2-propanedione, 1-(β-phenylbutyl)-3-phenyl-1,2-propanedione, 1-(α-halobutyl)-3-halophenyl-1,2-propanedione, and the like.

The acylmethyl ester reactant employed in the practice of the invention has the formula

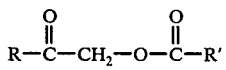

wherein R is an organic radical such as a saturated hydrocarbyl radical or an inertly substituted saturated hydrocarbyl radical and R' is hydrogen or an organic radical as specified for R. It is understood, of course, that R and R' may be different organic radicals in a given acylmethyl ester reactant.

Preferably R is an organic radical such as alkyl, cycloalkyl (e.g., cyclohexyl), aryl, haloalkyl, halocycloalkyl, haloaryl, alkoxyaryl, aryloxyaryl or combinations thereof, especially those radicals containing from 1 to about 18 carbon atoms. Most preferably, R is phenyl, halophenyl, alkyl or alkylphenyl, wherein the alkyl radical has from 1 to about 10 carbon atoms such as methyl, ethyl, propyl, n-butyl, t-butyl, n-hexyl, decyl, etc.; with phenyl, halophenyl or an alkylphenyl having from 7 to about 10 carbon atoms (e.g., tolyl, propylphenyl and t-butylphenyl, etc.) being especially preferred.

The radical R' is preferably hydrogen or a preferred organic radical as specified for R. More preferably R' is hydrogen, phenyl or an alkyl radical having from 1 to about 10 carbon atoms. Most preferably R' is hydrogen or an alkyl radical having from 1 to about 10 (especially from 1 to about 5) carbon atoms.

The aforementioned acylmethyl esters are sufficiently stable for prolonged storage prior to use.

The aforementioned acylmethyl ester reactants can be prepared by reacting an appropriate alpha-haloketone

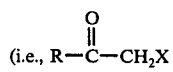

wherein the radical, R, is as previously defined and the halogen, X, is advantageously chlorine, bromine or iodine, preferably chlorine or bromine, most preferably chlorine) with an appropriate carboxylic acid of the formula

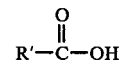

wherein R' is as previously defined or with a suitable salt of such carboxylic acid. Suitable salts include for example alkali metal salts, tertiary amine salts (such as salts of pyridine, trimethyl amine, etc.), quaternary ammonium salts (such as trimethylbenzylammonium salt, etc.), and salts of metals such as mercury or silver. Preferred salts are the alkali metal salts, especially the sodium and potassium salts. The reaction is conveniently performed pursuant to the procedure described in U.S. Pat. No. 3,526,634.

In a preferred embodiment of the invention the alpha-haloketone,

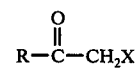

as defined hereinbefore, is employed as the initial ketone reactant in a multi-step one-pot process. In such one-pot process the initial step comprises contacting the alpha-haloketone with the carboxylic acid,

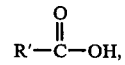

or a suitable salt thereof both as defined hereinbefore, preferably with at least about a stoichiometric amount of such acid or salt thereof. Such initial step of the one-pot process is generally conducted in a suitable solvent at elevated temperature, generally between about 50° C and about 120° C, under reflux conditions. The resulting reaction mixture is then reacted, with the chosen aldehyde reactant of the formula II pursuant to the reaction process defined hereinafter.

In the aforementioned initial step of such embodiment, suitable solvents include water and organic solvents such as an alcohol (e.g., methanol, ethanol, phenol, cyclohexanol), a cyclic ether (e.g., tetrahydrofuran, dioxane, etc.), halogenated hydrocarbon (e.g., carbon tetrachloride, chloroform, etc.), and similar common solvents, preferably water or an alkanol containing from 1 to about 6 carbon atoms, most preferably water, methanol or ethanol.

When, in the initial step of such one-pot process, a carboxylic acid is employed (as opposed to a salt thereof), it can act both as solvent and reactant. However, when a salt of one of the hereinbefore defined carboxylic acids is employed, it is generally desirable to use a solvent mixture (preferably in a 50:50 weight ratio) of both water and an organic solvent. Preferably such organic solvent is an alkanol containing from 1 to about 6 carbon atoms.

While not essential to the practice of the invention, it is generally advantageous to remove (generally by distillation) the majority of any organic solvent used in the reaction of the alpha-haloketone with the carboxylic acid (or salt thereof) before commencing the subsequent reaction with the hereinafter described aldehyde reactant. Such intermediate organic solvent removal generally simplifies the ultimate recovery of the final alpha-diketone reaction product.

In another embodiment of the invention, a ketone of the formula,

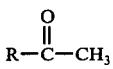

wherein R is as hereinbefore defined is employed as an initial reactant. Preferably in such embodiment R is a methyl radical, a phenyl radical, or a ring-substituted phenyl radical, such as ar-methyl-phenyl (i.e., tolyl), ar-bromo-phenyl, ar-, ar-dimethyl-phenyl, ar-(t-butyl)-phenyl, and like alkylphenyl, halophenyl, cycloalkyl-phenyl, etc., radicals. Most preferably in such embodiment R is a phenyl radical.

In such embodiment the corresponding alpha-haloketone

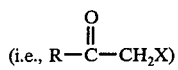

is prepared in situ by reacting the ketone with elemental halogen, $(X)_2$, pursuant to conventional halogenation techniques. As a general rule the halogen and the ketone are contacted in at least about stoichiometric amounts and at a temperature of between about 0° C and about 50° C (especially between about 0° and about 30° C). Preferably the halogen, $(X)_2$, is chlorine, bromine, or iodine, more preferably chlorine or bromine, most preferably chlorine. Purification of the resulting alpha-haloketone is not necessary before proceeding to the initial step of the aforementioned multi-step, one-pot process.

Common to all of the aforementioned embodiments of the invention (i.e., starting from (a) an acylmethyl ester, (b) an alpha-haloketone, or (c) a ketone) is a step comprising reacting the acylmethyl ester (or the reacted reaction mixture in cases (b) and (c)) with an aldehyde of the formula

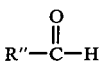

in the presence of an acid catalyst and water.

Optionally the reaction with the selected aldehyde can be conducted simultaneously with steam distillation of the reaction mixture. Such mode of operation is often advantageous in that it serves the dual function of separating the α-diketone reaction product from the reaction mixture and of accordingly driving the reaction forward toward completion.

In the aldehyde reactant R" is hydrogen or an organic radical as specified for R. Preferably R" is hydrogen or a preferred organic radical as specified for R. Most preferably R" is hydrogen, phenyl or an alkyl having from 1 to about 10 (especially from 1 to about 5) carbon atoms. Thus the most preferred aldehyde reactants include aldehydes such as formaldehyde, paraformaldehyde, acetaldehyde, propionaldehyde, 2-methylpropionaldehyde, n-valeraldehyde, n-heptanal, n-decanal, benzaldehyde, etc.

The ratio of reactants (i.e., aldehyde to either ketone, alpha-haloketone, or acylmethyl ester, depending upon the embodiment employed) is not critical to the practice of the invention. However, it is generally desirable to use at least about a stoichiometric amount of the aldehyde reactant based upon the number of moles of the ketone, α-haloketone or acylmethyl ester reactant (herein also referred to jointly as the "initial ketone reactant") initially employed. Naturally excess aldehyde reactant is often desirable to maximize the yield of the desired α-diketone. However, less than a stoichiometric amount of the aldehyde can also be advantageously employed. Thus, for example, an amount of the selected aldehyde between about 0.5 and about 5, preferably between about 1 and about 5, more preferably between about 1 and about 3, most preferably between about 1.1 and about 2, moles of aldehyde per mole of the selected initial ketone reactant is advantageously employed.

The aforementioned reaction with the aldehyde is conducted in the presence of an acid catalyst. The specific acid catalyst used and the amount employed is not particularly critical to the practice of the invention so long as sufficient acidity of the reaction mixture is maintained (e.g., a maximum pH of about 2, preferably about 1, most preferably about 0.5) to promote the formation of the desired α-diketone at an acceptable rate. For example, suitable acid catalysts include organic and inorganic acids (especially the inorganic acids) exhibiting pKa values of about 3.0 or less.

Examples of suitable inorganic acid catalysts include arsenic, chromic, hydrobromic, hydrochloric, hydroiodic, iodic, nitric, periodic, o-phosphoric, pyrophosphoric, selenic, selenious, sulfuric, sulfurous, etc.

Examples of suitable organic acid catalysts include o-aminobenzosulfonic, benzosulfonic, bromoacetic, bromobenzoic, chloroacetic, o-chlorobenzoic, α-chlorobutyric, α-chloropropionic, cyanoacetic, γ-cyanobutyric, o-, m- or p-cyanophenoxyacetic, cyanopropionic, cyclopropane-1:1-dicarboxylic, dichloroacetic, dichloroacetylacetic, 2,2- or 2,5-dihydroxybenzoic, dihydroxymaleic, dihydroxytartaric, dinicotinic, fluorobenzoic, o-iodobenzoic, maleic, malonic, naphthalenesulfonic, oxalic, o-phthalic, picric, quinolinic, trichloroacetic, trifluoroacetic, 2,4,6-trihydroxybenzoic, 2,4,6-trinitrophenol, and the like.

Preferably the organic or inorganic acid catalyst exhibits a pKa value of about 2.0 or less. Examples of such preferred inorganic acid catalysts include chromic, hydrochloric, hydrobromic, hydroiodic, iodic, nitric, periodic, pyrophosphoric, selenic, sulfuric, sulfurous, etc. Examples of such preferred organic acid catalysts include benzosulfonic, cyclopropane-1:1-dicarboxylic, dichloroacetic, difluoroacetic, dihydroxymaleic, dihydroxytartaric, maleic, naphthalenesulfonic, oxalic, picric, trichloroacetic, trifluoroacetic, 2,4,6-trihydroxybenzoic, 2,4,6-trinitrophenol, and the like.

Most preferably the acid catalyst is hydrochloric, hydrobromic, sulfuric, or sulfurous acid.

The amount of acid catalyst employed depends upon a variety of factors such as the reaction rate desired, the strength of the acid employed, the nature of the particular reactants involved, the amount and nature of the solvent or solvents (if any) employed, and so forth. However, as a general rule, at least about 0.05, preferably between about 0.1 and about 10, more preferably between about 0.25 and about 5, most preferably between about 0.5 and about 5 moles of acid catalyst per mole of the initial ketone reactant, is advantageously employed.

Similarly, the amount of water employed is not particularly critical to the practices of the invention so long as a sufficient amount (e.g., at least about 0.05 mole per mole of initial ketone reactant) is present to promote formation of the desired α-diketone at an acceptable rate. However, as a general rule between about 0.5 and about 1000, preferably between about 1 and about 500, most preferably between about 10 and 100, moles of water are advantageously employed per mole of the initial ketone reactant.

The means of introducing the acid catalyst and water to the process is not particularly critical. Thus for example in an embodiment wherein an α-haloketone is generated in situ or wherein hydrogen halide is otherwise generated as a reaction by-product, residual hydrogen halide remaining in the reaction vessel can serve as the acid catalyst in the reaction with the aldehyde reactant. Similarly when water is used as a solvent in a prior step of an embodiment of the invention or when steam distillation is employed, further water addition for the reaction with the aldehyde is not generally necessary.

The temperature at which the reaction with the aldehyde is conducted is likewise not particularly critical so long as it is sufficiently high to provide a satisfactory reaction rate and sufficiently low to avoid significant thermal decomposition (and corresponding unsatisfactorily low yields) of the derived α-diketone product. Generally, reaction temperatures between about 50° C and about 120° C, preferably between about 70° C, and about 110° C, are satisfactory from both such standpoints.

The pressure at which the process of the invention is conducted (i.e., for all steps of the various embodiments) is not critical. However, operation of the particular step involved at the autogenous pressure accompanying that particular step under the other relevant conditions selected is convenient and therefore preferred.

Recovery of the desired α-diketone reaction product from the reaction mixture can be accomplished by conventional methods. For example, it can be removed during the course of the reaction with the aldehyde reactant via concurrent steam distillation as previously mentioned. In such case the product is contained within the organic layer which can be decanted from the accompanying aqueous layer. Alternatively a separate distillation step (steam or otherwise) may be employed after the reaction is terminated. Or, the reaction mixture can be cooled and the resulting organic layer can be decanted. In addition, conventional solvent extraction techniques may be employed, either alone or in conjunction with (i.e., before, after or both) conventional distillation techniques.

In those instances wherein (a) the initial ketone reactant is a ketone or an alpha-haloketone, (b) the reaction with the carboxylic acid or salt thereof is conducted in the presence of an organic solvent, and (c) the majority of such organic solvent is not removed prior to commencing the reaction with the aldehyde reactant, the organic mixture recovered (by whatever means) will often contain a significant quantity of such organic solvent. In such instances a subsequent solvent-solvent extraction process is often conveniently employed to separate such solvent from the desired α-diketone product, particularly where the characteristics of the individual solvent and diketone concerned render separation by conventional distillation techniques impractical.

The following examples are presented to further illustrate the practice of the invention.

EXAMPLE 1

1-Phenyl-1,2-Propanedione from α-Chloroacetophenone, Sodium Acetate and Paraformaldehyde A mixture containing 199 g. (1 mole) of α-bromoacetophenone, 90 g. (1.05 moles) of sodium acetate, 1000 ml. of water and 800 ml. of ethanol is heated at reflux at between 65° and 70° C for three hours. A distillation head is attached to the reaction mixture and 670 ml. of liquid is distilled. The temperature at the beginning of the distillation is 70° C and gradually increases during the distillation to a final temperature of 95° C. The volume of liquid in the reaction is kept approximately constant by periodic addition of water. Following this distillation, 36 g. (1.2 moles) of paraformaldehyde and 390 ml. of concentrated HCl are added to the residue and the mixture is subjected to steam distillation. As the distillation pot approaches dryness, an additional 50 ml. of concentrated HCl and 50 ml. of water are added. An aqueous liquid and a water immiscible liquid, 1900 ml. total, distills together at a temperature of about 100° C. Steam distillation is discontinued when the distillate is faint green-yellow in color. The distillate is extracted with methylene chloride. The methylene chloride is dried (MgSO$_4$) and evaporated on the rotary evaporator to yield 129 g. (0.872 mole) (87 percent yield) of pure 1-phenyl-1,2-propanedione. The identity of the product is verified by comparison with a commercially obtained sample.

EXAMPLE 2

1-Phenyl-1,2-Propanedione from α-Bromoacetophenone, Sodium Acetate and Paraformaldehyde Pursuant to the procedure of Example 1, one mole of α-bromoacetophenone is reacted with 1.05 moles of sodium acetate in an aqueous ethanol solution. A 1.2 mole portion of paraformaldehyde is then reacted with the resulting mixture in the presence of 3.6 moles of aqueous HCl. The resulting product is verified to be 1-phenyl-1,2-propanedione.

While the invention has been described with reference to particular examples and embodiments, such examples and embodiments are illustrative only. They should therefore not be understood as limiting the instantly claimed invention.

What is claimed is:

1. A process for the preparation of an alpha-diketone of the formula,

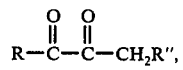

comprising contacting an acylmethyl ester of the formula,

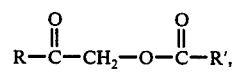

with an aldehyde of the formula,

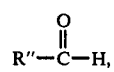

in the presence of an amount of acid catalyst and an amount of water and under reaction conditions, which amounts and conditions are sufficient to cause reaction of the ester with the aldehyde to form the diketone, wherein the aforementioned formulas R is an alkyl, cycloalkyl or aryl radical; an inertly substituted alkyl, cycloalkyl, or aryl radical; or a combination thereof; and R' and R" are individually hydrogen or a radical as specified for R.

2. The process of claim 1 wherein R is phenyl, halophenyl, alkyl or alkylphenyl, wherein the alkyl radical has from 1 to about 10 carbon atoms; R' is hydrogen, phenyl or an alkyl radical having from about 1 to about 10 carbon atoms; and R" is hydrogen, phenyl or an alkyl radical having from 1 to about 10 carbon atoms.

3. The process of claim 1 wherein (a) between about 0.5 and about 5 moles of the aldehyde is present per mole of the acylmethyl ester, (b) at least about 0.05 mole of acid catalyst is present per mole of the acylmethyl ester, (c) at least about 0.05 mole of water is present per mole of the acylmethyl ester, and (d) the process is conducted at a temperature between about 50° and about 120° C.

4. A process for the preparation of an alpha-diketone of the formula,

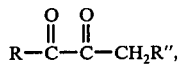

comprising (a) an initial process step which comprises reacting an alpha-haloketone of the formula,

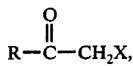

with a carboxylic acid of the formula,

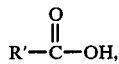

or a salt thereof and (b) a second process step which comprises reacting the reaction mixture resulting from the initial process step with an aldehyde of the formula,

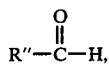

under conditions, and in the presence of amounts of an acid catalyst and water, which amounts and conditions are sufficient to cause formation of the alpha-diketone; wherein in the aforementioned formulas R is an alkyl, cycloalkyl, or aryl radical; an inertly substituted alkyl, cycloalkyl, or aryl radical; or a combination thereof; and R' and R" are individually hydrogen or a radical as specified for R.

5. The process of claim 4 wherein R is phenyl, halophenyl, alkyl or alkylphenyl, wherein the alkyl radical has from 1 to about 10 carbon atoms; R' is hydrogen, phenyl or an alkyl radical having from 1 to about 10 carbon atoms; R" is hydrogen, phenyl or an alkyl radical having from 1 to about 10 carbon atoms; X is bromine or chlorine; and the carboxylic acid or salt thereof is an alkali metal salt of the carboxylic acid.

6. The process of claim 4 wherein the alpha-diketone is 1-phenyl-1,2-propanedione; the alpha-haloketone is alpha-chloroacetophenone or alpha-bromoacetopenone; the carboxylic acid or salt thereof is sodium acetate; the aldehyde is paraformaldehyde; and the acid catalyst is hydrochloric acid.

7. The process of claim 4 wherein both steps of the process are carried out in a single reaction vessel without intermediate product purification between the initial process step and the second process step.

8. The process of claim 7 wherein (a) at least about a stoichiometric amount of the carboxylic acid or salt thereof is employed per mole of alpha-haloketone in the initial process step, (b) between about 0.5 and about 5 moles of the aldehyde is present in the second process step per mole of the initially charged alpha-haloketone, (c) at least about 0.05 mole of acid catalyst is present in the second process step per mole of the alpha-haloketone initially charged, (d) at least about 0.05 mole of water is present in the second process step per mole of the initially charged alpha-haloketone, and (e) both steps of the process are conducted at a temperature between 50° and about 120° C.

9. The process of claim 4 the alpha-haloketone of the formula

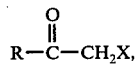

is prepared in situ by reacting a ketone of the formula,

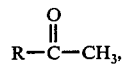

with a halogen, (X)$_2$, wherein R is a methyl radical, a phenyl radical or a ring-substituted phenyl radical.

10. The process of claim 9 wherein the process is carried out in a single reaction vessel without intermediate product purification following the in situ alpha-haloketone preparation and without intermediate product purification between the initial process step and the second process step.

11. A process for the preparation of an alpha-diketone of the formula,

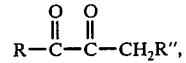

comprising contacting an acylmethyl ester of the formula,

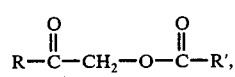

with an aldehyde of the formula,

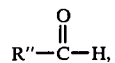

at a temperature of between about 50° and about 120° C and in the presence of (a) at least about 0.05 mole, per mole of the acylmethyl ester, of an organic or inorganic acid catalyst exhibiting a pKa of less than about 3.0 and (b) at least about 0.05 mole of water per mole of the acylmethyl ester; wherein, in the formulas, R is an alkyl, cycloalkyl, or aryl radical; an inertly substituted alkyl, cycloalkyl or aryl radical; or a combination thereof; and R' and R" are individually hydrogen or a radical as specified for R.

12. The process of claim 11 conducted at a maximum pH of 2.

13. The process of claim 12 wherein:
   a. R is phenyl, halophenyl, alkyl or alkylphenyl wherein the alkyl radical contains from 1 to about 10 carbon atoms;
   b. R' is hydrogen, phenyl or an alkyl radical having from 1 to about 10 carbon atoms; and
   c. R" is hydrogen, phenyl or an alkyl radical having from 1 to about 10 carbon atoms.

14. Th process of claim 13 wherein the acid catalyst is hydrochloric acid, hydrobromic acid, sulfuric acid or sulfurous acid.

15. The process of claim 14 wherein R is phenyl and wherein the aldehyde is paraformaldehyde.

16. The process of claim 4 wherein (a) both process steps are conducted at a temperature of between about 50° and about 120° C and (b) the second process step is conducted at a maximum pH of 2.

17. The process of claim 16 wherein
   a. between about 0.1 and about 10 moles of acid catalyst is employed per mole of alpha-haloketone;
   b. the acid catalyst is an organic or inorganic acid selected from the group consisting of chromic, hydrochloric, hydrobromic, hydriodic, iodic, nitric, periodic, pyrophosphoric, selenic, sulfuric, sulfurous, benzosulfonic, cyclopropane-1:1-dicarboxylic, dichloroacetic, difluoroacetic, dihydroxymaleic, dihydroxytartaric, maleic, naphthalenesulfonic, oxalic, picric, trichloroacetic, trifluoroacetic, 2,4,6-trihydroxy-benzoic, and 2,4,6-trinitrophenol; and
   c. between about 0.5 and about 1000 moles of water is employed per mole of alpha-haloketone.

18. The process of claim 17 wherein the alpha-diketone is 1-phenyl-1,2-propanedione; the alpha-haloketone is alpha-chloroacetophenone or alpha-bromoacetophenone; the carboxylic acid or salt thereof is sodium acetate; the aldehyde is paraformaldehyde; and the acid catalyst is hydrochloric acid.

* * * * *

UNITED STATES PATENT AND TRADEMARK OFFICE
CERTIFICATE OF CORRECTION

PATENT NO. : 4,107,210
DATED : August 15, 1978
INVENTOR(S) : Edward R. Freiter

It is certified that error appears in the above-identified patent and that said Letters Patent are hereby corrected as shown below:

Columns 3 and 4 should be deleted and the attached columns 3 and 4 substituted therefor, but will apply to the Grant only.

Column 2, line 20, delete and insert

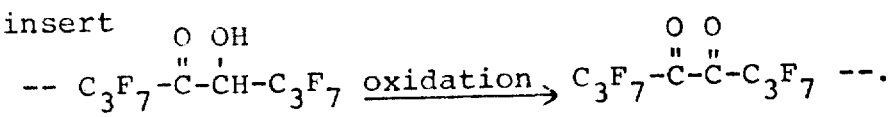

Column 11, line 1, before "acid" insert -- an --.

Column 11, line 5, after "wherein" insert -- in --.

Column 12, line 1, delete "alpha-bromoacetope-" and insert -- alpha-bromoacetophe- --.

Column 12, line 22, after "Claim 4" insert -- wherein --.

UNITED STATES PATENT AND TRADEMARK OFFICE
CERTIFICATE OF CORRECTION

PATENT NO. : 4,107,210

DATED : August 15, 1978

INVENTOR(S) : Edward R. Freiter

It is certified that error appears in the above-identified patent and that said Letters Patent are hereby corrected as shown below:

Column 13, line 17, delete "Th" and inser -- The --.

*Signed and Sealed this*

*Twelfth Day of June 1979*

[SEAL]

Attest:

RUTH C. MASON
*Attesting Officer*

DONALD W. BANNER
*Commissioner of Patents and Trademarks*

Finally, condensation reactions between alpha-hydroxyl ketones and aldehydes have also been reported. Such reactions are exemplified by equations (12) and (13).

Lengenbeck, German Patentschrift 10621 (1955)    (12)

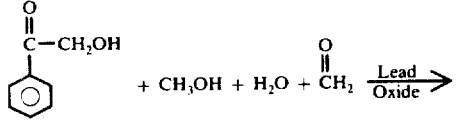

alpha-hydroxy acetophenone

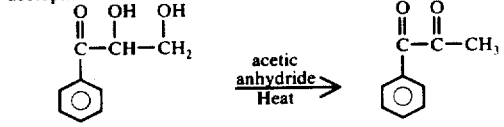

α,β-dihydroxy propiophenone 1-phenyl-1,2-propanedione

Dermer, U.S. PAT. No. 2,799,707 (1957)    (13)

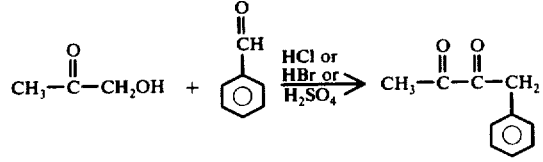

acetol    benzaldehyde    1-phenyl-2,3-butanedione

Unfortunately, however, the various known methods of synthesizing alpha-diketones are often commercially unsatisfactory by virtue of low yields; high energy requirements; slow reaction rates; limited availability, chemical instability, or high cost of the required reactants or catalyst; complex reaction procedures; complex purification procedures; toxicity of reactants, catalyst or by-products; etc.

It is therefore desirable to provide a process for preparing alpha-diketones in high yield (e.g., 50 to 80 percent or more) from readily available, stable and economical raw materials via a simple process and without the need for (or production of) highly toxic raw materials, catalyst or intermediates.

SUMMARY OF THE INVENTION

This invention is a process for the preparation of alpha-diketones which comprises contacting an acyl-methyl ester of a carboxylic acid with an aldehyde in the presence of an acid catalyst and water under conditions sufficient to cause reaction of the ester with the aldehyde to form the diketone. Such process is represented by the following equation:

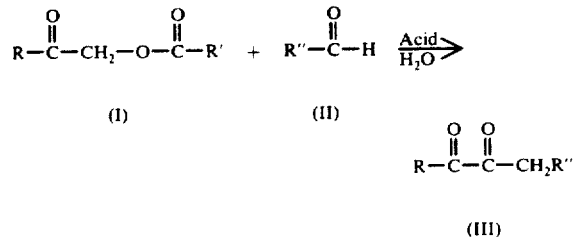

wherein R is an organic radical such as a saturated hydrocarbyl radical or an inertly substituted saturated hydrocarbyl radical and R' and R'' are individually hydrogen or a radical as specified for R.

As used herein the term "saturated hydrocarbyl" includes radicals such as alkyl, cycloalkyl, aryl and combinations thereof and excludes olefinically or acetylenically unsaturated radicals, such as alkenyl, alkynyl, and the like.

As used herein the term "combinations thereof" (when referring to a prior listing of radicals) means that a more complex radical, composed of the relatively less complex radicals listed, may be used. Thus, for example, when the list of radicals include alkyl, cycloalkyl and aryl radicals, "combinations thereof" include radicals such as alkylaryl, alkylcycloalkyl, alkylarylalkyl, arylcycloalkyl, cycloalkylarylalkyl, and the like.

The term "inertly substituted saturated hydrocarbyl" includes radicals such as halohydrocarbyl, nitrohydrocarbyl, hydrocarbyloxyhydrocarbyl, halohydrocarbylthiohydrocarbyl, hydrocarbyloxyhalohydrocarbyl, etc., wherein the hydrocarbyl radicals are saturated hydrocarbyl radicals as hereinbefore defined.

An embodiment of the invention of particular interest is a process for the preparation of alpha-diketone (formula III) which employs an alpha-haloketone

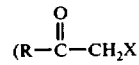

wherein R is as previously defined and X is halogen) as an initial reactant. In such process the alpha-haloketone is first reacted with a carboxylic acid

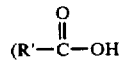

wherein R' is as previously defined), or a salt thereof. Then the resulting reaction mixture is reacted with an aldehyde (II), under conditions sufficient to cause reaction, in the presence of an acid catalyst and water, to form the alpha-diketone.

The resulting alpha-diketones produced pursuant to the various embodiments of this invention are useful as intermediates for pharmaceuticals, dyestuffs and perfumes.

DETAILED DESCRIPTION OF INVENTION

The process of the invention comprises preparation of an alpha-diketone by contacting an acylmethyl ester with an aldehyde in the presence of an acid catalyst and water under conditions sufficient to cause reaction of the ester with the aldehyde to form the diketone.

The alpha-diketones produced by the process of the invention are substituted 1,2-propanediones having the formula

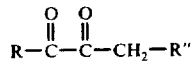

wherein R and R'' are as further defined hereinafter in conjunction with the acylmethyl ester and aldehyde reactants.

Such alpha-diketones include (a) 1-substituted-1,2-propanediones wherein R'' is hydrogen and R is an organic radical as hereinafter defined and (b) 1,3-disubstituted-1,2-propanediones wherein R and R'' are or-